US00PP27020P2

(12) United States Plant Patent
Vila

(10) Patent No.: US PP27,020 P2
(45) Date of Patent: Aug. 2, 2016

(54) ***ZANTEDESCHIA* PLANT NAMED 'ANGEL WHITE ONE'**

(50) Latin Name: *Zantedeschia aethiopica*
Varietal Denomination: White Angel One

(71) Applicant: Oriol Cotet Vila, Barcelona (ES)

(72) Inventor: Oriol Cotet Vila, Barcelona (ES)

(73) Assignee: GLADIOLUS BREEDERS GROUP, Barcelona (ES)

( * ) Notice: Subject to any disclaimer, the term of this patent is extended or adjusted under 35 U.S.C. 154(b) by 259 days.

(21) Appl. No.: 13/998,507

(22) Filed: Nov. 6, 2013

Related U.S. Application Data

(60) Provisional application No. 61/797,702, filed on Dec. 13, 2012.

(51) Int. Cl.
*A01H 5/02* (2006.01)

(52) U.S. Cl.
USPC ..... Plt./490

(58) Field of Classification Search
USPC ..... Plt./490, 263.1
See application file for complete search history.

(56) References Cited

PUBLICATIONS

UPOV-PLUTO: Plant Variety Database Jul. 22, 2015; cultivar name 'White Angel One'.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Zantedeschia aethiopica* plant named 'White Angel One', characterized by its compact plant habit, its exhibits numerous stems and clumps for division, its broad leaves, its very broad spathes that are pure white in color with minimal fading with age, its good resistance to *Erwinia caratovora*, and its vigorous growth habit.

2 Drawing Sheets

Botanical classification: *Zantedeschia aethiopica.*
Cultivar designation: 'White Angel One'.

BACKGROUND OF THE INVENTION

The present invention relates to a new and distinct cultivar of *Zantedeschia aethiopica*, and is hereinafter referred to by the cultivar name 'White Angel One'. 'White Angel One' represents a new herbaceous perennial grown for use as a landscape plant.

The new cultivar was derived from a controlled breeding program by the Inventor in Barcelona, Spain. The objective of the breeding program was to produce a new cultivar of *Zantedeschia* with large, pure white flowers. The Inventor made a cross in May of 2002 between unnamed proprietary plants in the Inventor's breeding program; reference no. GBCA001 as the female parent and reference no. CAAGUILA002 as the male parent. The Inventor selected 'White Angel One' in April of 2004 as a single unique plant amongst the seedlings that resulted from the above cross.

Asexual propagation of the new cultivar was first accomplished by the Inventor by tuber division in October of 2004 in Barcelona, Spain. Asexual propagation by tuber division has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'White Angel One' as a new and unique cultivar of *Zantedeschia.*

1. 'White Angel One' exhibits a compact plant habit.
2. 'White Angel One' exhibits numerous stems and shoots for division.
3. 'White Angel One' exhibits broad leaves.
4. 'White Angel One' exhibits very broad spathes that are pure white with minimal fading with age.
5. 'White Angel One' has shown good resistance to Erwinia caratovora.
6. 'White Angel One' exhibits a vigorous growth habit.

The female parent of 'White Angel One', GBCA001, differs from 'White Angel One' in having a taller plant height and spathes that creamy white in color. The male parent of 'White Angel One', CAAGUILA002, differs from 'White Angel One' in having a less vigorous growth habit, in producing less inflorescences, and in having spathes that are creamy white in color. 'White Angel One' can be most closely compared to the cultivars 'Little Anna' (not patented), and 'Polaris' (not patented. 'Little Anna' is similar to 'White Angel One' in producing numerous shoots and in having a wide spadix. 'Little Anna' differs from 'White Angel One' in having spathes that are creamy white and narrower and in having a shorter plant height and longer petioles. 'Polaris' is similar to 'White Angel One' in having good resistance to *Erwinia caratovora* and in its suitability for production in warm regions. 'Polaris' differs from 'White Angel One' in having spathes that are creamy white, in having a shorter production period, in being less compact, and in having leaf blades that are a more intense color of green.

BRIEF DESCRIPTION OF THE DRAWING

The accompanying colored photograph illustrate the overall appearance and distinct characteristics of the new *Zant-*

*edeschia*. The photographs was taken of a plant about 7 months in age as grown outdoors in a greenhouse in Barcelona, Spain.

Figure 1:
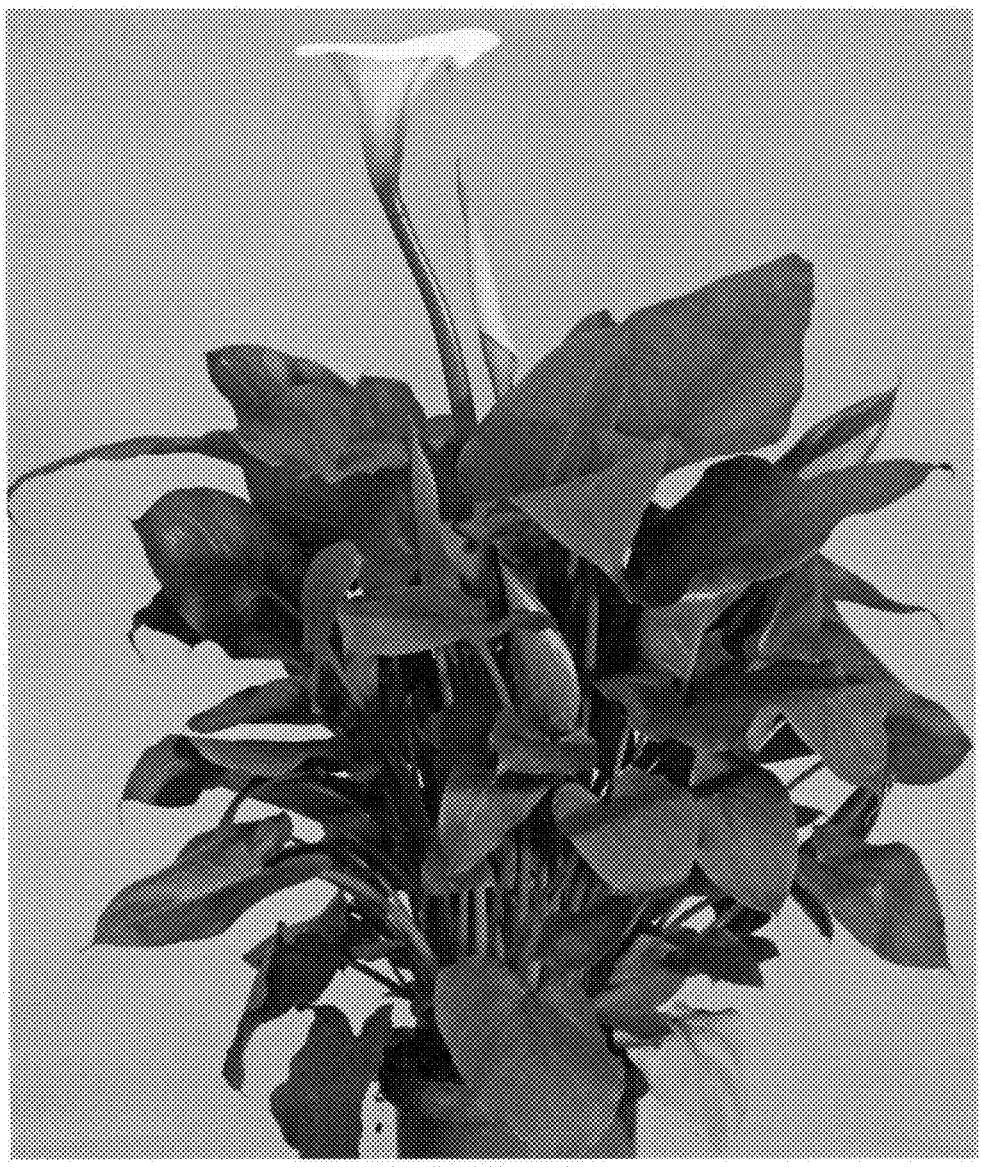

The photograph in FIG. 1 provides a side view of 'White Angel One' in bloom.

Figure 2:
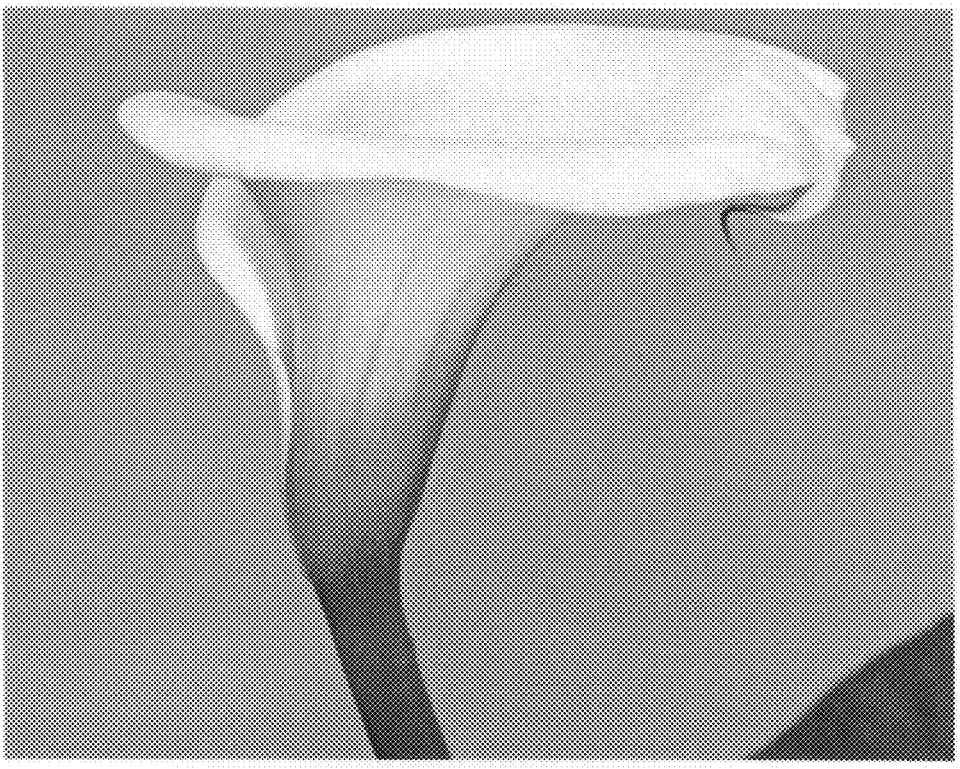

The photograph in FIG. 2 provides a close-up view of a flower of 'White Angel One'.

Figure 3:
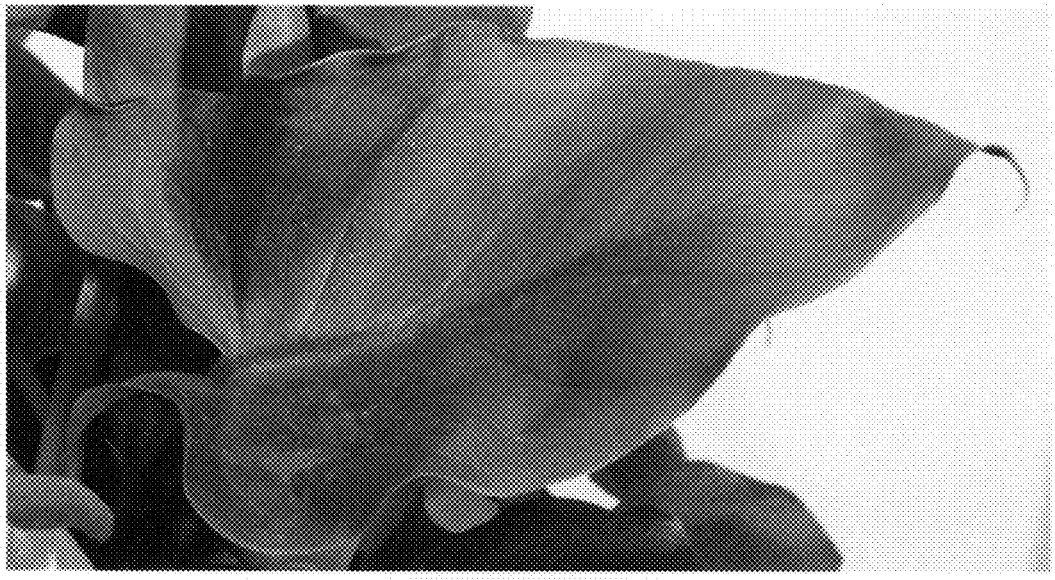

The photograph in FIG. 3 provides a close-up view of a leaf of 'White Angel One'.

The colors in the photographs may differ slightly from the color values cited in the detailed botanical description, which accurately describe the colors of the new *Zantedeschia*.

DETAILED BOTANICAL DESCRIPTION OF THE PLANT

The following is a detailed description of 7 month-old plants of the new cultivar as grown in a greenhouse in 3-liter containers. Plant were grown under average day temperatures of 15° to 25° C. and average night temperatures of 4° to 10° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From March to mid May in Barcelona, Spain.

*Plant type*.—Perennial, evergreen with sufficient moisture.

*Plant habit*.—Clump forming, compact, upright with multiple stems.

*Height and spread*.—Average of 64 cm in height to top of inflorescences (45 cm to top of foliage), average of 50 cm in spread.

*Hardiness*.—Tropical plant, cold hardy at least in U.S.D.A. Zone 8, good high temperature tolerance.

*Diseases*.—Has shown good resistance to *Erwinia caratovora*.

*Root description*.—Thick and fibrous.

*Branching habit*.—Clump forming plant with basal stems, no lateral branches.

*Propagation*.—Tuber division.

*Growth rate*.—Vigorous; produces 8 harvestable shoots per year and 18 clumps for division.

Stem description (peduncle):

*Shape*.—Triangular in cross-section.

*Stem color*.—A blend of 143C and 144B, 144C at the base.

*Stem size*.—An average of 57.8 cm in length and 1.4 to 1.6 mm in diameter.

*Stem surface*.—Glabrous.

*Stem aspect*.—Held nearly erect, average angle 5° (straight upright=0°).

*Stem strength*.—Moderate.

*Stem number*.—An average of 8 per plant.

Foliage description:

*Leaf shape*.—Cordate to sagittate.

*Leaf division*.—Single.

*Leaf base*.—Hastate.

*Leaf apex*.—Aristate, curled downwards.

*Leaf venation*.—Pinnate.

*Leaf margins*.—Entire, undulate.

*Leaf attachment*.—Petiolate.

*Leaf arrangement*.—Alternate, growing directing from base.

*Leaf surface*.—Upper and lower surface glabrous and smooth, moderately leathery, and slightly glossy.

*Leaf substance*.—Slightly leathery.

*Leaf color*.—Young upper surface; 143A, young lower surface;143B to 143C, mature upper surface; a blend of N137B and 147A but darker, mature lower surface; a blend of 143A and 146A.

*Leaf size*.—Mature leaves, an average of 23.4 cm in length and 14 cm in width.

*Leaf quantity*.—Average of 4 per stem.

*Petioles*.—Average of 29.3 cm in length, 0.9 cm in width, 0.8 cm in height, and a color slightly darker than 143A.

Flower description:

*Inflorescence type*.—Spathes with spadices held above the foliage.

*Inflorescence size*.—An average of 10.5 cm in height (excluding peduncle), 11.0 cm in depth, and 10.8 cm in width.

*Lastingness of inflorescence*.—An average of 4.5 weeks on plant and 2.5 weeks as a cut flower, persistent.

*Spathe*.—Broad ovate in shape, strongly cupped with revolute margin, smooth and glabrous on all surfaces, slightly thick and leathery, arrangement; straight on top of peduncle, about 11 cm in length and 10.8 cm in width, apex; aristate to mucronate, base; sheathing, color when opening front side; a blend of 155C and 157D and rear side; N144C to N144D and 150B to 150C towards margins and apex, color when fully opened; front side NN155D, rear side NN155D and a blend of 143C, 144B and 144C at the base, color does not fade.

*Inflorescence no.*.—An average of 8 per plant per season.

*Spadix*.—Cylindrical in shape tapering towards the top, placed straight on top of the peduncles, apex and base; obtuse, an average of 5.8 cm in length and 1.1 cm in width, immature color; 12A, mature color; 13C, upper 75% portion contains male flowers and female flowers are at the base, smooth surface.

*Peduncle*.—Triangular in cross-section, 57.8 cm in length and an average of 1.4 to 1.6 mm in width, moderate in strength, color; a blend of 143C and 144B with base 144C, surface is glabrous.

*Flower fragrance*.—Faint, sweet and pleasant.

*Flower no.*.—Male; an average of 700, female; an average of 60.

*Flower type*.—Male; irregularly oblong in shape, no perianth or sepals, an average of 1 mm in diameter and 0.5 mm in depth, female; rounded in cross section, single, an average of 3 mm in diameter and 2 mm in depth.

Reproductive organs:

*Gynoecium*.—Ovaries 150C and 150D in color, stigmas 150D in color.

*Androecium*.—Anthers 12B in color, pollen moderate in quantity and 11D in color.

*Fruit/seed*.—No fruit or seed have been observed to date.

It is claimed:

1. A new and distinct cultivar of *Zantedeschia* plant named 'White Angel One' as herein illustrated and described.

* * * * *